United States Patent [19]

Hawkinson, Jr. et al.

[11] Patent Number: 4,516,068
[45] Date of Patent: May 7, 1985

[54] TIRE DEFECT TESTER

[75] Inventors: Raymond P. Hawkinson, Jr., Minneapolis; Dennis W. Newman, Saint Paul, both of Minn.

[73] Assignee: Paul E. Hawkinson Company, Minneapolis, Minn.

[21] Appl. No.: 488,760
[22] PCT Filed: Apr. 16, 1982
[86] PCT No.: PCT/US82/00479
 § 371 Date: Apr. 18, 1983
 § 102(e) Date: Apr. 18, 1983
[87] PCT Pub. No.: WO83/03681
 PCT Pub. Date: Oct. 27, 1983

[51] Int. Cl.³ ............................................. G01R 31/12
[52] U.S. Cl. ......................................................... 324/54
[58] Field of Search ............................. 324/54; 73/146

[56] References Cited

U.S. PATENT DOCUMENTS 1,779,907 10/1930 Dye ........................................ 324/54
3,465,242 9/1969 Gruetzmacher et al. ............. 324/54

Primary Examiner—Stanley T. Krawczewicz
Attorney, Agent, or Firm—Merchant, Gould, Smith, Edell, Welter & Schmidt

[57] ABSTRACT

An improved biased electrode (54) as used in a tire defect tester (12) is the subject of this patent application. The electrode (54) is movable between a first position located within a circle circumscribed by the beads (28) of a tire (26) being tested and a second position received in a cavity between the sidewalls (30) of the tire (26) in engagement with an underside of the tread portion (38) of the tire (26). The electrode (54) includes at least one, and, in a preferred embodiment, two, elongated member (72). The member (72) is pivotally mounted so that, as the electrode (54) is moved from its first to its second position, a first arm portion (80) will engage the underside of the tread portion (38) of the tire (26) and cause the element (72) to pivot so that it is in engagement with the underside of the tread portion (38) substantially along the length of the element (72). During operation, an electric charge is given to the electrode (54), thereby imposing a potential across the electrode (54) and a neutral reference electrode (36) positioned on the other side of the tread portion (38) of the tire (26). If defects exist in the portions of the tire (26) sandwiched between the electrodes (36, 54), an arc will occur thereacross.

6 Claims, 5 Drawing Figures

4,516,068

TIRE DEFECT TESTER

TECHNICAL FIELD

The invention of the present patent application refers broadly to the field of apparatus and equipment for testing tires for defects such as punctures and other structural damage which might have been inflicted upon the tread portion of the tire. More specifically, the invention deals with an improved electrode used in a system for testing wherein an electrical potential is imposed across the electrode and a neutral reference electrode and wherein, when a defect is detected, arcing will occur through the defect between the two electrodes. In a preferred embodiment of the invention, the biased electrode is configured for easy insertion into the annular cavity formed between the sidewalls of the tire and into engagement with the underside of the tread portion of the tire.

BACKGROUND OF THE INVENTION

Tires available for commercial sale are generally one of two types: new tires and tires which have been retreaded. Because of the ever escalating cost of new tires, the retreading market has become more appealing to many consumers.

The retreading of used tires serves a significant economical function. Not only does it provide a less expensive product to the consuming public, but it also limits waste which results from the discarding of tire carcasses.

Prior to the conduct of retreading operations upon a used tire carcass, it is necessary to ascertain if any foreign objects are embedded in the tread portion of the tire or if any cracks, fissures, or holes exist therein. The prior art has typically relied upon visual inspection in order to make this determination. If such defects are found to exist, they are cured prior to continuing with retreading operations.

Visual inspection for such defects tends to be slow and time consuming. More importantly, however, this method of searching for defects is, at best, unreliable. With this method, a tire is rotated on a mounting stand, and an inspector visually observes the tread portion of successive tires as they pass beneath his gaze. Although a trained eye might detect defects which would not be apparent to the untrained observer, the monotony of observing the tread portions of successive tires make it difficult, after a period of observation, to reliably spot such defects.

Additionally, some defects are so minute that they escape the detection of even a trained, experienced observer. Nevertheless, even defects of this nature can cause problems if the tires are retreated without proper treatment being given to correct the defects.

In an attempt to solve some of the problems inherent in visual inspection, other types of testing have been devised. One such method involves over inflating the tire to a degree and either immersing the tire in a fluid or applying a fluid to the outer surface thereof. A leak of air through an orifice or fisher can be detected visually more readily by the observation of a bubbling effect which will occur at the location of the defect.

Non-visual systems have come into use in order to augment visual inspection. Ultrasonic systems have, in recent years, become used more frequently for aiding in the detection of defects as previously discussed.

Although the use of fluids to facilitate detection of defects and systems such as ultrasonic systems have made detection searches more reliable, many problems yet exist. Where many tires are processed, it is important to conduct an inspection as expeditiously as possible. Inspections conducted even with the use of fluids and ultrasonic detectors have done little to accomplish more expeditious processing during inspection.

Recently, a system wherein the tread portion of a tire is sandwiched between a pair of electrodes across which a high voltage electrical potential is generated has been discovered. With this system, if objects such as nails are embedded in the tread portion of the tire or if defects such as orifices or fissures exist, the voltage applied across the electrodes will cause arcing at the point of foreign object or defect. In one such system of which applicant is aware, a tire is mounted for rotation with the circumferential tread portion passing between the electrodes. The apparatus by which the invention is practiced includes an electronics package whereby as a defect is detected by arcing across the electrodes, rotation of the tire will be stopped. Pinpointing the location of the defect is, thereby, facilitated. The location of the defect can be indicated on the surface of the tire, and the tire can be subsequently repaired prior to performing retreading operations. Tires can, thereby, be processed relatively quickly and reliably.

Existing structures by which this high voltage testing procedure is accomplished do, however, in some respects, limit the speed at which tires can be processed. Typically, the construction of a tire is such that the beads (or radially innermost edges of the sidewalls) are spaced axially from each other a smaller distance than are the greater portions of the sidewalls. Consequently, insertion of an electrode into engagement with the underside of the tread portion of the tire requires the prying apart of the beads in order to allow entry of an electrode which has a dimension in a direction axially with respect to the tire, as great as the width of the tread portion thereof. An electrode so dimensioned is desirable in order to maximize the area of the tread portion which is actually tested.

In consequence of this need to pry the beads open to a degree, delays can be encountered. Particularly, in enterprises conducting large scale retreading operations involving large numbers of tires, the total time delay involved on a daily basis can be rather significant.

The invention of the present application is an electrode uniquely configured in order to minimize the time involved in testing any one particular tire unit. It is an electrode specifically designed for use in a system as described above wherein the tread portion of a tire is passed between two electrodes across which a high voltage potential exists. The electrode is configured so that no time need be expended in prying the beads apart in order to facilitate entry of the electrode into the annular cavity within the tire and into engagement with the underside of the tread portion thereof.

SUMMARY OF THE INVENTION

The invention of the present application is a biased electrode for use with apparatus for testing tires wherein the apparatus includes structure by which a tire can be mounted for rotation, a neutral reference electrode which can be brought into engagement with the outer tread portion of the tire, and a controller unit which provides a charge to the biased electrode to create an electrical potential across the biased electrode and the neutral reference electrode. The biased electrode includes an elongated member which is mounted for rotation about a pivot. The point about which the member pivots divides the member into first and second arm portions. The member is disposed for movement between a first position wherein it is within a circle defined by the beads of the tire and a second position wherein it is substantially in engagement with the underside of the tread portion. In its first position, the element is normally biased to an orientation wherein the first arm portion is closer to the tread portion than is the second arm portion. When the elongated element is in its first position, the first arm portion extends at an angle to a plane defined by the tread portion of the tire. As the member is moved from its first position to its second position, an extremity of the first arm portion will, first, engage the underside of the tread portion. Such engagement and continued movement of the point of pivoting toward the tread portion will cause the member to be pivoted until it is in engagement with the underside of the tread portion along substantially its full length.

The extremity of the first arm portion which first engages the underside of the tread portion of the tire can be provided with a bearing, rotatable across the tread portion of the tire in a direction generally perpendicular to the direction of movement of the tread portion about the axis with respect to which the tire rotates. The change of frictional damage to the tread portion can, thereby, be minimized.

To a similar end, the second arm portion of the elongated member can be provided with a plurality of bearings aligned along the length of the second arm portion. These bearings can be made rotatable across the tread portion of the tire in the direction of movement of the tread portion about the axis of rotation of the tire.

In a preferred embodiment, the electrode can be provided with a pair of elongated members which are disposed for pivoting about a common axis. Each of the members can be configured for operation as in the case of a single member electrode as previously discussed. When a pair of elongated members are used, however, they would be adapted for pivoting in opposite directions as the electrode were moved from its first position to its second position in engagement with the tread portion of the tire. By so adapting the electrode, it could be made to extend virtually across the full width of the tire's tread portion.

In view of the construction of the electrode in accordance with the present invention, it can be brought into engagement with the underside of a tire tread portion without delays which might be incurred because of the need to pry the beads of the tire away from one another. The invention of the application is, therefore, an electrode for use in tire testing as thusly improved. More specific features and advantages obtainable in view of those features will become apparent with reference to the detailed description of the invention, appended claims, and drawing figures.

DETAILED DESCRIPTION OF THE INVENTION

Figure 1:
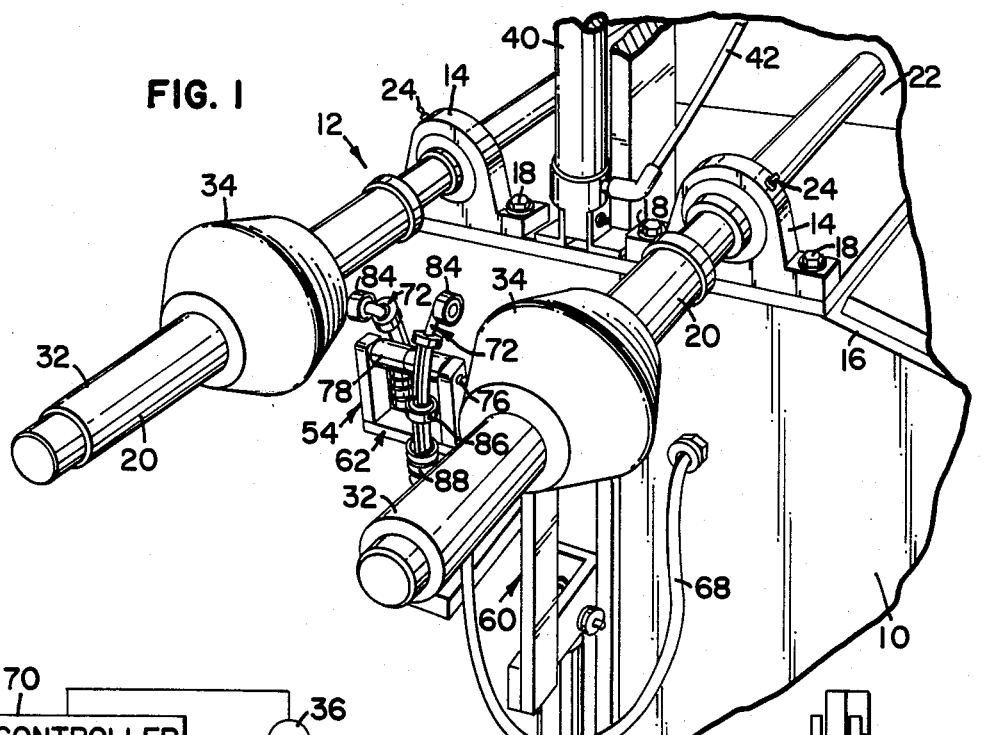
FIG. 1 is a view in perspective illustrating a portion of a tire testing apparatus incorporating the improved electrode of the present patent application.

Referring now to the drawings wherein like reference numerals denote like elements throughout the several views, FIG. 1 illustrates a portion of the cabinet 10 of a tire defect tester 12 with which the electrode invention of the present application is typically used. A pair of journal bearings 14 are shown mounted atop the cabinet 10 proximate one edge 16 thereof. The journal bearings 14 are secured to the cabinet 10 by appropriate means such as bolt/washer arrangements 18.

Journaled within each of the bearings 14 is a drive roller 20 extending, at one end, from a motor housing 22, through the journal bearing 14, and beyond the edge 16 of the tester apparatus cabinet 10. In order to insure adequate lubrication of the journal bearings 14, they can be provided with zerk fittings 24 through which lubricative material can be pumped. One or both of the drive rollers 20 can be rotationally driven by motor means (not shown) within the motor housing 22. If both rollers 20 are driven, they would be driven in a common direction in order to augment each other in imparting rotational motion to a tire 26 which can be seated with the beads 28 of the sidewalls 30 in engagement with the roller surfaces 32.

In order to position the tire 26 in proper axial location with respect to the drive rollers 20, enlarged hub members 34 having axial dimensions similar to the distance between the beads 28 of a tire 26 can be provided, one of the hub members 34 being positioned on each of the drive rollers 20 at a similar distance from the edge of the cabinet 16. It will be understood that a particular tester apparatus unit 12 would be designed for a particular type of tire. Consequently, knowing the distance between the beads 28 of the particular type of tire for which the tester is designed, the hubs 34 can be given an appropriate dimension in an axial direction.

Figure 3:
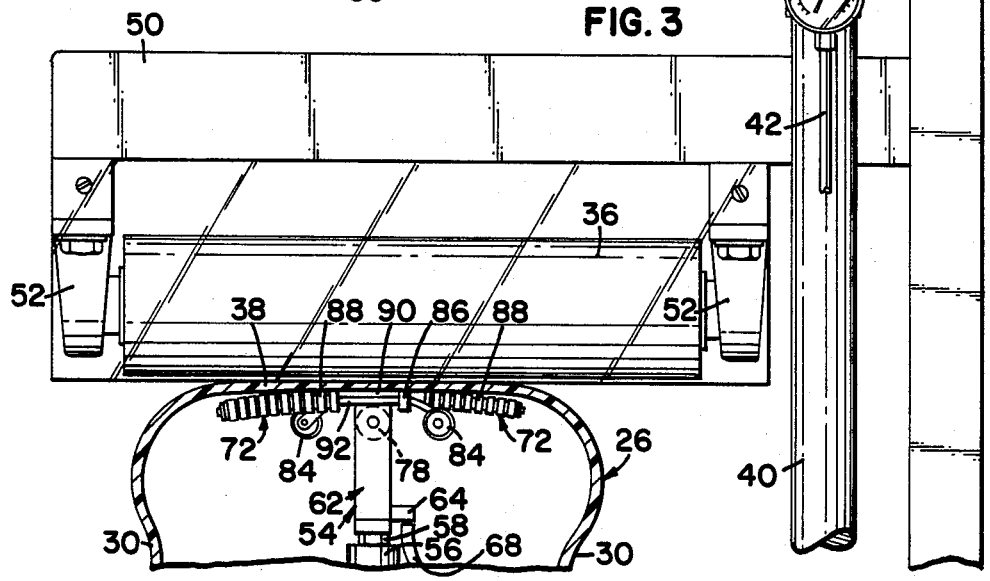
FIG. 3 is a front elevational view of the apparatus of FIG. 1 illustrating, in section, a tire being tested.

When a tire 26 is to be tested, it would be seated on the drive rollers 20 with its beads 28 in engagement with the outer surfaces 32 of those rollers 20 and with the hub members 34 extending into the annular cavity defined between the sidewalls 30 of the tire 26. With the tire 26 so seated in position for being driven in a rotational motion by the drive rollers 20, a first electrode 36, which can have a neutral polarity for reference, can be brought downwardly to a position which would be in engagement with the outer surface of the tread portion 38 of the tire 26 as best seen in FIG. 3. Appropriate means such as a pneumatic cylinder 40 having hose couplings 42 entering the cylinder 40 on either side of a piston slidably disposed therein can be used for this purpose. Pressures within the cylinder 40 can be monitored by providing an appropriate gauge 44.

The electrode 36 can be operatively connected to the cylinder 40 by a shaft 46 extending from the cylinder 40 and appropriate linkage structure 48. A rack portion 50 of the linkage structure 48 can include a pair of flanges 52 between which the electrode 36 can be rotatably journaled. The electrode 36 can, therefore, rotate freely when in engagement with the outer surface of the tread portion 38 of the tire 26 while the tire 26 is rotated about an axis.

As shown in FIG. 1, a biased electrode 54 is positioned axially, with respect to the axis about which the tire 26 is rotated, proximate the axial center lines of the hubs 34. Means are provided for moving the electrode 54, in the embodiment illustrated, between two vertically spaced positions. As in the case of the neutral reference electrode 36, the means by which the biased electrode 54 is moved can comprise a pneumatic cylinder 56 whose piston is linked to the electrode 54 by a piston rod 58 and other appropriate linkage structure 60.

The first position of the electrode 54 is the lower of the two positions, and this position would be achieved when the piston rod 58 is withdrawn into the pneumatic cylinder 58. When the electrode 54 is in this position, its upper extremity would be at the height approximately the same as that at which are the upper extremities of the hubs 34.

When a tire 26 is seated on the drive rollers 20, the circle defined by the beads 28 will provide that that portion of the circle bridging the distance between the rollers 20 is arced upwardly from the surfaces 32 of the rollers 20. Consequently, the electrode 54, in its first position, will be positioned within the circumference of the circle defined by the beads 28.

Since the axial position of the electrode 54 with respect to the axis of rotation of the tire 26 is proximate the center line of the hubs 34, it will also be disposed axially intermediate the beads 28. Consequently, when air is introduced into a lower chamber of the pneumatic cylinder 56 below the piston to drive the piston, and, consequently, the electrode 54, upwardly, the electrode 54 will not be obstructed from entering an annular cavity defined between the sidewalls 30 of the tire 26.

Figure 4:
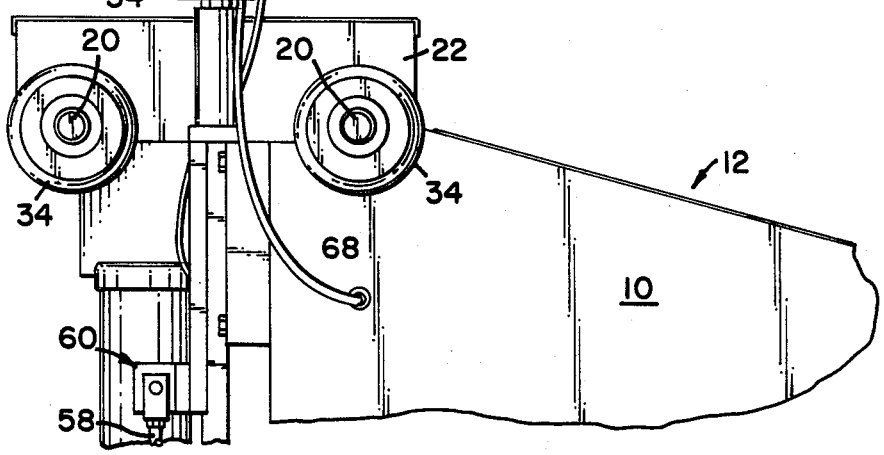
FIG. 4 is a side elevational view of the apparatus of FIG. 1 without a tire mounted for testing and with the electrodes in engagement.

As previously discussed, the second position of the biased electrode 54 is spaced upwardly, in the embodiment illustrated, from its first position. In its second position, the electrode 54 engages the underside of the tread portion 38 of the tire 26. As seen in FIG. 4, when the neutral reference electrode 36 is in its lower position and the biased electrode 54 is in its second, upper position, the two electrodes 36, 54 substantially engage one another. As seen in FIG. 3, when a tire 26 is seated on the drive rollers 20, therefore, a segment of the tread portion 38 of the tire 26 will be sandwiched between the electrodes 36, 54.

Figure 5:
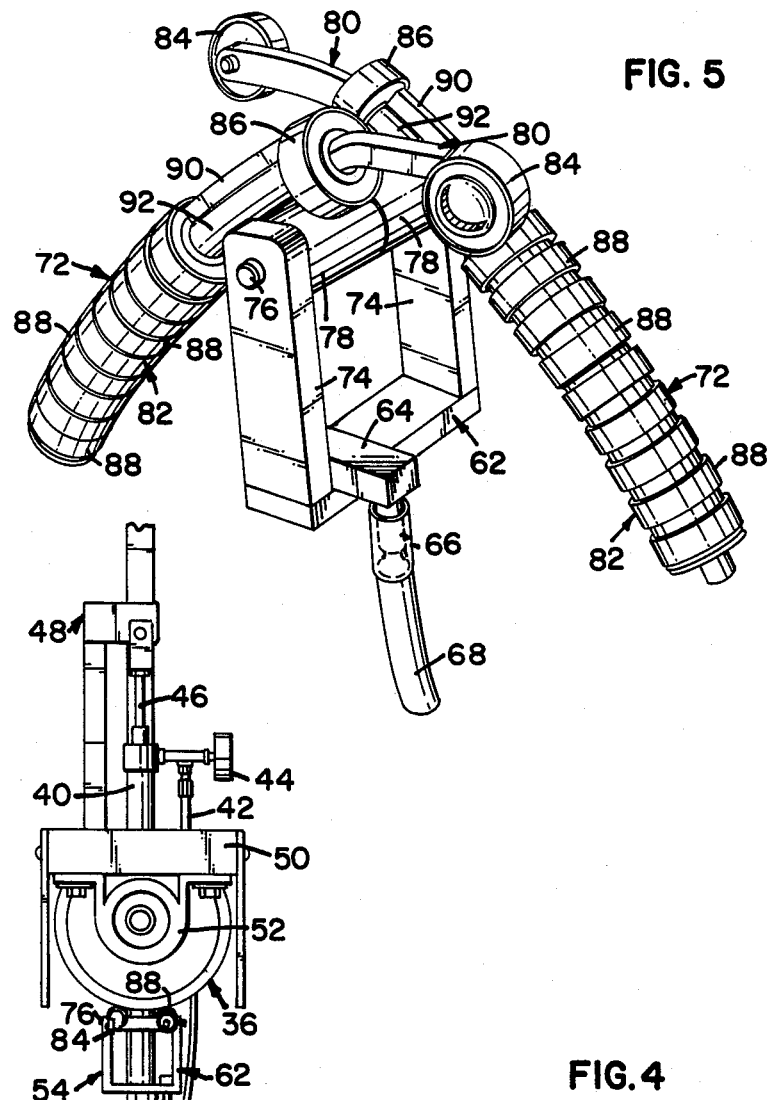
FIG. 5 is a view in perspective of an electrode in accordance with the invention of the present application.

Referring then to FIG. 5 for the specific structural features of the biased electrode 54, a yoke 62 is mounted to the structure 60 linking the electrode 54 to the pneumatic cylinder 56. A boss 64 extends laterally from the yoke 62 and carries a connector 66 which, in FIG. 5, is shown as protruding downwardly from the boss 64.

An electrical cable 68 is mated to the connector 66. The cable 68, at its other end, is attached to a controller unit 70 within the cabinet 10 of the testing apparatus 12. The controller 70, through the cable 68, imparts an electrical charge to the connector 66, the boss 64, the yoke 62, and, in turn, all other portions of the electrode 54 are hereinafter defined, since all elements of the electrode 54 are electrically conductive. In order to so provide, the components of the electrode 54 are manufactured of one of a number of materials having appropriate conductivity characteristics.

At least one elongated member 72 is pivotally mounted to the yoke 62 proximate remote ends of arms 74 thereof. As shown in FIG. 5, two pivotally mounted, elongated members 72 are appropriate.

A shaft 76 is made to extend across the gap between the remote ends of the arms 74 and are secured thereto in any conventional manner. The shaft 76 carries a pair of sleeves 78, each sleeve 78 being free to rotate about the shaft 76. Each sleeve 78 is, in turn, rigidly secured to one of the elongated members 72 at a location along the length of the member 72.

The location along the member 72 at which it is secured to its respective sleeve 78 bifurcates the member 72 into first and second arm portions 80, 82. As seen in FIG. 5, first arm portions 80 extend upwardly from the yoke 62 and have a single bearing 84 mounted for rotation at extremities thereof. A second bearing 86, defining a plane generally transverse to a plane defined by the bearing 84 at the upper extremity of the first arm portion 80, is illustrated as being positioned intermediate the extremity and the axis of pivoting.

The second arm portions 82 are seen as extending generally downwardly. The second arm portions 82 are provided with a plurality of bearings 88 aligned along the greater part of their lengths. These bearings 88 are positioned in orientations similar to that of the bearing 86 carried by the respective first arm portion 80 intermediate the extremity of said first arm portion 80 and the axis of pivoting.

A spacer bar 90 is secured to a shaft 92 of each elongated member 72 and straddling the first and second arm portions 80, 82 thereof. The spacer bar 90 serves two functions: first, it serves to hold the bearings 86, 88 apart at a location at which the shaft 92 can be fixedly secured to one of the sleeves 78; and, second, it serves to provide a relatively continuous surface from a remote end of a second arm portion 82, axially along a segment of the circumferences of the bearings 88 carried by the second arm portion 82, across the spacer bar 90, and to the bearing 86 carried by the first arm portion 80 intermediate the extremity thereof and the axis of pivoting. Consequently, when the electrode 54 is in its second position in engagement with the underside of the tread portion 38 of the tire 26, a substantially continuous surface will be either in engagement with the tread portion 38 or closely spaced from the tread portion 38.

As seen in the figures, the elongated members 72 are provided with a measure of arcuity. Because of the weight of the bearings 88 carried by the second arm portions 82, the members 72 will be biased so that the first arm portions 80 are, when the electrode 54 is in its first position, more closely proximate the tread portion 38 of the tire 26 to be tested. In view of the arcuity of the members 72, the extremities of the first arm portions 80 will be spaced axially with respect to the axis about which the tire 26 is rotated, each first arm portion 80 defining an angle oblique to that segment of the tread portion 38 of the tire 26 immediately above the electrode 54.

When a tire 26 is to be tested, the neutral reference electrode 36, is by operation of its respective pneumatic cylinder 40, raised to its upper position. Similarly, the biased electrode 54 is, by operation of its respective pneumatic cylinder 56, lowered to its first position between the hubs 34 carried by the drive rollers 20. With the electrodes 36, 54 in these positions, a tire 26 is placed on the drive rollers 20 with the hubs 34 axially between the beads 28 of the tire 26.

With the tire 26 seated in this manner, the neutral electrode 36 is lowered into engagement with the upper surface of the tread portion 38 of the tire 26 as seen in FIG. 3. In a similar manner, the pneumatic cylinder 56 by which the height of the biased electrode 54 is adjusted is operated to move that electrode 54 toward its second position. As the electrode 54 approaches the underside of the tread portion 38 of the tire 26, the extremities of the first arm portions 80, and, specifically, the bearings 84 carried at those extremities, will, first, engage the underside of the tread portion 38. As the electrode 54 is continued to be urged closer toward the tread portion 38, the bearings 84 will roll across the tread portion 38 in a direction generally perpendicular to the direction of movement of the tread portion 38 when the tire 26 is rotated about its axis of rotation. Damage which might be incurred by frictional engagement absent a bearing is, thereby, eliminated.

The electrode 54 will continue to be moved toward the tread portion 38 until it achieves its second position wherein the elongated members 72, substantially along their lengths, are in engagement with the underside of the tread portion 38 of the tire 26. As can be seen, because of the orientations of the other bearings 86, 88, only rolling friction will occur between the electrode 54 and the tread portion 38 once the tire 26 is made to rotate.

The dimension of the electrode 54 in a direction axially relative to the axis of rotation of the tire 26 when the electrode 54 is in its second position in engagement with the underside of the tread portion 38 can be greater than the dimension, in the same direction, between the beads 28 of the tire 26. The axial dimension of the electrode 54 when the electrode 54 is in its first position, however, can be smaller than the distance between the beads 28 in order to facilitate easy insertion of the electrode 54 into the cavity defined between the sidewalls 30 of the tire 26 and into engagement with the underside of the tread portion 38 thereof.

Figure 2:
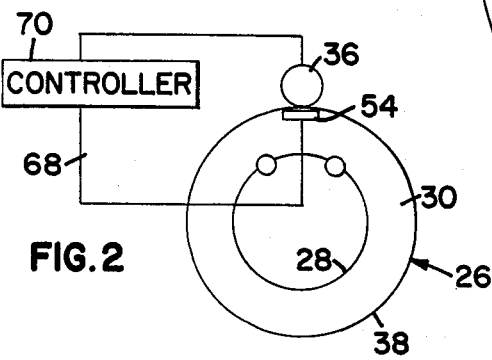
FIG. 2 is a schematic view illustrating the apparatus, portions of which are illustrated in FIG. 1.

The positioning of the various elements of the tester 12 during actual operation is illustrated schematically in FIG. 2. The electrodes 36, 54 are in position sandwiching a segment of the tread portion 38 of the tire 26 therebetween. The controller unit 70 functions to impose a bias upon the lower electrode 54 and to generate, thereby, a potential across the electrodes 36, 54. If a foreign body such as a nail is embedded in the tread portion 38 of the tire 26, or if orifices or fissures exist in that tread portion 38, arcing will occur across the electrodes 36, 54 to indicate the defect. The defect location can be marked on the tire 26, and, after the tire 26 is removed from the tester 12, the defects can be repaired prior to completion of retreading operations.

Numerous characteristics and advantages of the invention have been set forth in the foregoing description. It will be understood, of course, that this disclosure is, in many respects, only illustrative. Changes can be made in details, particularly in matters of shape, size, and arrangement of parts without exceeding the scope of the invention. The invention's scope is defined by the language in which the appended claims are expressed.

What is claimed is:

1. In combination with apparatus for testing tires for structural defects and damage in the nature of holes in the tread portion thereof, wherein the apparatus includes means for mounting and rotating the tire, and a rotatable first electrode engagable with the outer tread portion of the tire:
   (a) a second electrode movable between a first position within a circumference defined by the tire beads and a second position engaging an underside of the tread portion, comprising:
      (i) an elongated member having a pivot bifurcating said member into first and second arm portions;
      (ii) means mounting said member for rotation about said pivot; and
      (iii) means normally biasing said member to an orientation spaced at an oblique angle relative to the tread portion with said first arm portion more closely proximate the underside of the tread portion than is said second arm portion;
      (iv) wherein, as said second electrode is moved from its first position to its second position, said first arm portion engaging the underside of the tread portion of the tire causes said elongated member to rotate about said pivot until said member is in engagement, along its full dimension along its axis of elongation, with the underside of the tread portion; and
   (b) means generating an electrical potential across said first and second electrodes.

2. The combination of claim 1 wherein an extremity of said first arm portion is provided with a bearing rotatable across the tread portion of the tire generally perpendicular to the movement of the tread portion about an axis with respect to which the tire is mounted for rotation.

3. The combination of claim 1 wherein said second arm portion is provided with a pluraltiy of bearings, aligned along its length, rotatable across the tread portion of the tire in the direction of movement of the tread portion about the axis with respect to which the tire is mounted for rotation.

4. A biased electrode for use with apparatus for detecting defects in tires, wherein the apparatus includes means for mounting and rotating a tire, a neutral reference electrode engagable with the outer tread portion of the tire, and a controller unit providing a charge to said biased electrode and an electrical potential across said biased electrode and the reference electrode, comprising:
   (a) A pair of elongated members disposed for pivoting about a common axis, said axis dividing each of said members into first and second arm portions;
   (b) means for positioning said members in first positions within a circumference circumscribed by the tire beads and axially intermediate the beads, wherein said members are biased about said common axis to orientations wherein said first arm portions extend in a direction generally toward the neutral reference electrode; and
   (c) means for selectively urging said members to second positions substantially in engagement with an underside of the tread portion of the tire immediately opposite the neutral reference electrode;
   (d) wherein, as said members are urged from their first to their second positions, said first arm portions first engage the underside of the tread portion of the tire and, as said common axis moves farther toward the tread portion, said members pivot about said common axis so that said second arm portions swing away from each other in opposite directions axially with respect to an axis about which the tire is made to rotate, and into engagement with the underside of the tread portion of the tire.

5. A biased electrode in accordance with claim 4 wherein the controller includes means for electrically polarizing said biased electrode with a positive charge.

6. A biased electrode in accordance with claim 4 wherein extremities of said first arm portions are, when said members are in their first positions, spaced from each other axially with respect to the axis about which the tire is made to rotate.

* * * * *